US012799444B2

(12) United States Patent
Lee et al.

(10) Patent No.: US 12,799,444 B2
(45) Date of Patent: Nov. 17, 2026

(54) MICROCARRIER BASED-4 DIMENSIONAL CELL CULTURE APPARATUS AND METHOD FOR MONITORING CELL CULTURE USING THE SAME

(71) Applicant: UNIVERSITY-INDUSTRY COOPERATION GROUP OF KYUNG HEE UNIVERSITY, Yongin-si (KR)

(72) Inventors: EunAh Lee, Seoul (KR); Wook Park, Suwon-si (KR); Tae Woo Kim, Hwaseong-si (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 1072 days.

(21) Appl. No.: 17/799,297

(22) PCT Filed: Mar. 5, 2021

(86) PCT No.: PCT/KR2021/002775
§ 371 (c)(1),
(2) Date: Dec. 29, 2022

(87) PCT Pub. No.: WO2021/177792
PCT Pub. Date: Sep. 10, 2021

(65) Prior Publication Data

US 2023/0112108 A1 Apr. 13, 2023

(30) Foreign Application Priority Data

Mar. 6, 2020 (KR) ........................ 10-2020-0028471

(51) Int. Cl.
*C12M 1/12* (2006.01)
*C12M 1/00* (2006.01)
*C12M 1/34* (2006.01)

(52) U.S. Cl.
CPC ............ *C12M 25/16* (2013.01); *C12M 29/18* (2013.01); *C12M 41/30* (2013.01)

(58) Field of Classification Search
CPC ....... C12M 25/16; C12M 29/18; C12M 41/30
(Continued)

(56) References Cited

U.S. PATENT DOCUMENTS 4,322,296 A 3/1982 Fan et al.
4,748,123 A * 5/1988 Birch ..................... C12M 27/20 435/293.1
(Continued)

FOREIGN PATENT DOCUMENTS

JP 3275411 B2 4/2002
JP 2004236553 A * 8/2004
(Continued)

OTHER PUBLICATIONS

JP-2011172533-A Machine English Translation Description (Year: 2011).*
(Continued)

*Primary Examiner* — Michael L Hobbs
*Assistant Examiner* — Lenora A Abel
(74) *Attorney, Agent, or Firm* — Sughrue Mion, PLLC

(57) ABSTRACT

The present invention relates to a low specific gravity microcarrier-based cell culture apparatus and a method of monitoring cell culture using the same. More particularly, the present invention relates to four-dimensional cell culture that enables monitoring of the growth state of cells by reflecting a time factor in three-dimensional cell culture and
(Continued)

is capable of stable cell expansion culture by minimizing change in cell characteristics.

3 Claims, 5 Drawing Sheets

(58) Field of Classification Search
USPC ........................................................ 435/293.1
See application file for complete search history.

(56) References Cited

U.S. PATENT DOCUMENTS

| | | | | |
|---|---|---|---|---|
| 4,892,818 | A | 1/1990 | Ramp | |
| 5,256,616 | A | 10/1993 | Heller et al. | |
| 2009/0035848 | A1 * | 2/2009 | Hickey | C12M 33/14 435/296.1 |
| 2012/0009645 | A1 | 1/2012 | Oh et al. | |
| 2016/0046898 | A1 | 2/2016 | Lee et al. | |
| 2019/0144820 | A1 | 5/2019 | Oh et al. | |

FOREIGN PATENT DOCUMENTS

| | | | | |
|---|---|---|---|---|
| JP | 2011172533 | A * | 9/2011 | C12M 25/14 |
| KR | 10-1975100 | B1 | 5/2019 | |
| WO | 2004020572 | A2 | 3/2004 | |
| WO | 2017/176055 | A1 | 10/2017 | |

OTHER PUBLICATIONS

JP-2004236553-A Machine English Translation (Year: 2004).*
International Search Report of PCT/KR2021/002775 dated Jun. 2, 2021 [PCT/ISA/210].
Extended European Search Report issued May 7, 2024 in European Application No. 21764495.4.
Notice of Allowance dated Oct. 18, 2022, which issued during the prosecution of Korean Patent Application No. 10-2020-0028471.

* cited by examiner

[FIG. 1]
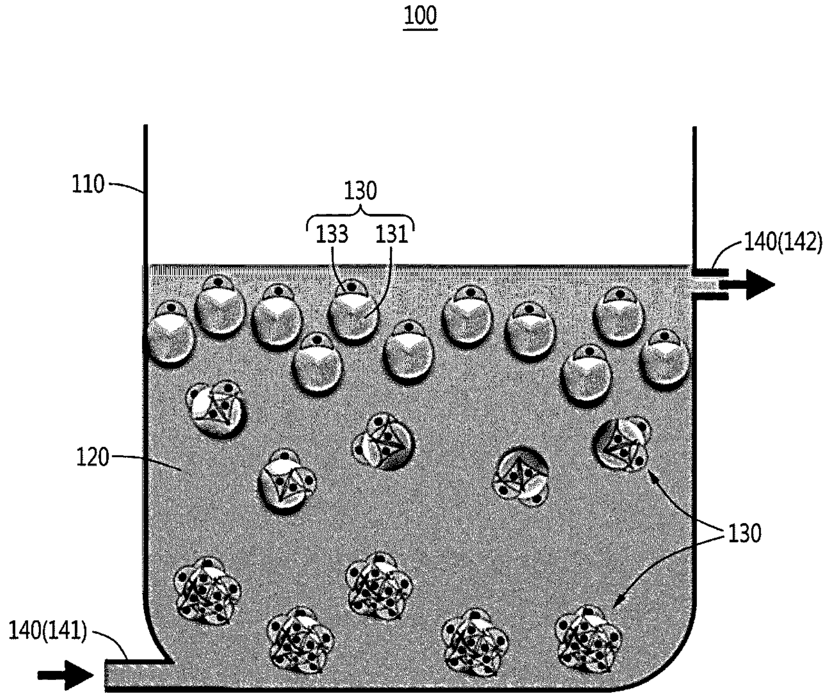
[FIG. 2A]
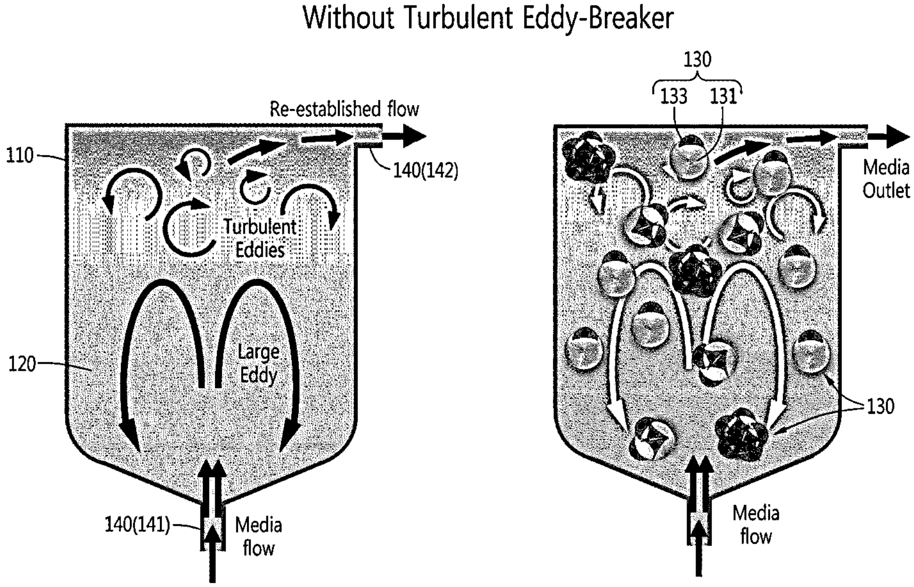

[FIG. 2B]
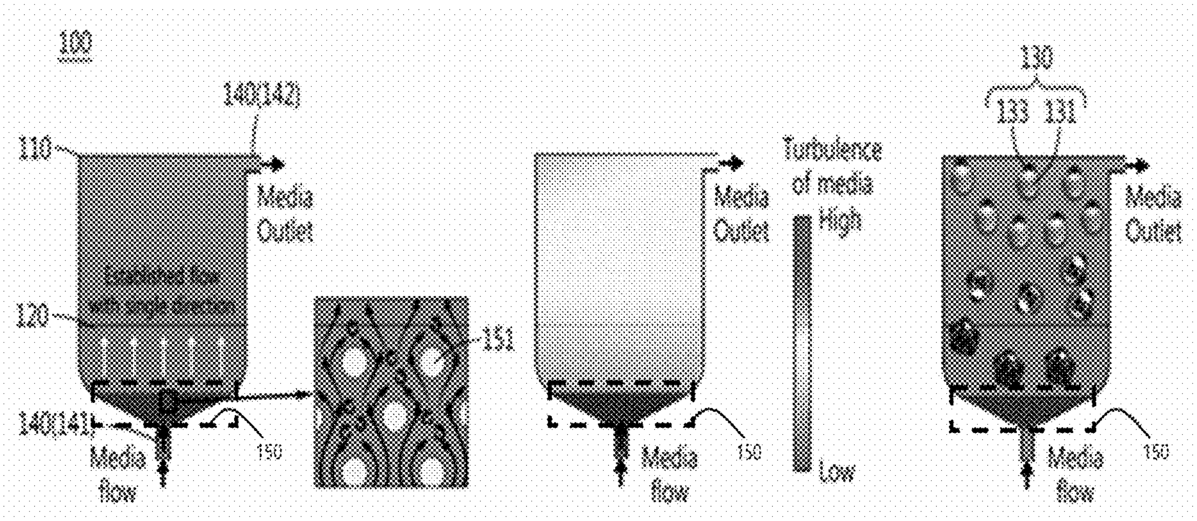
[FIG. 3A]
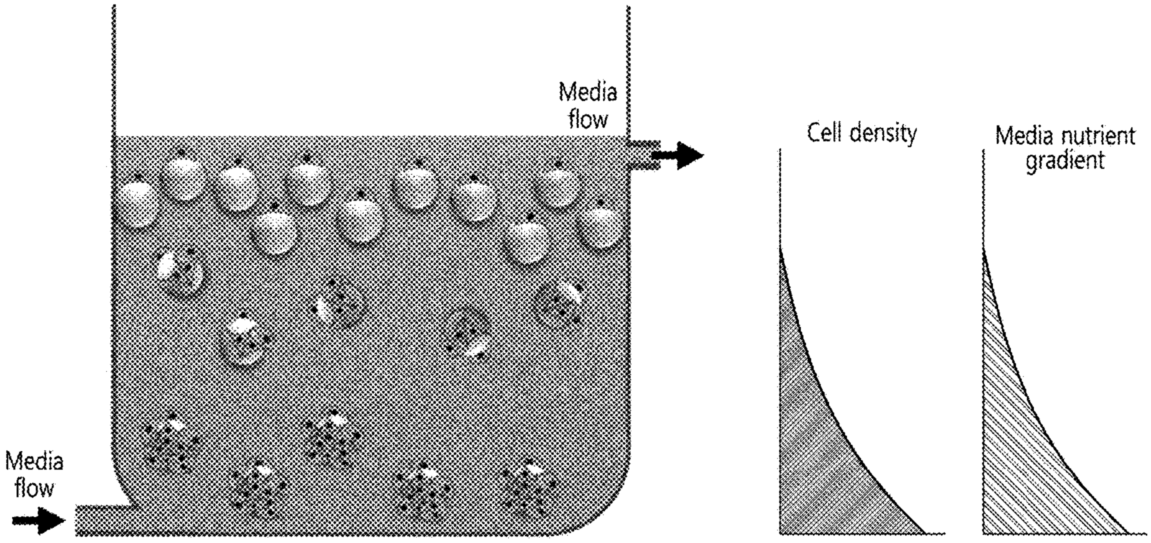

[FIG. 3B]
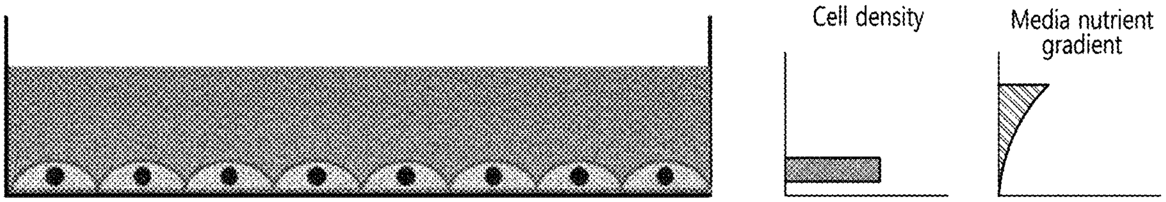
[FIG. 4]
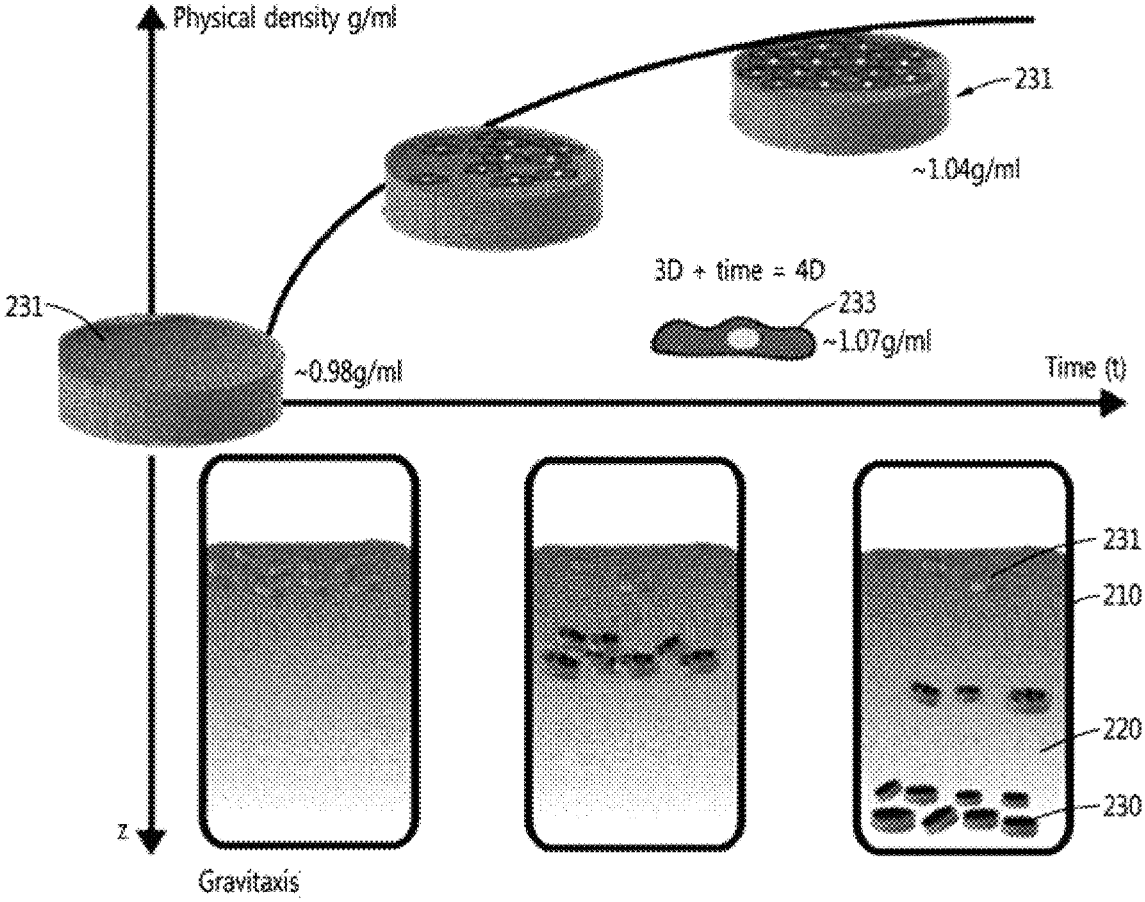

[FIG. 5]
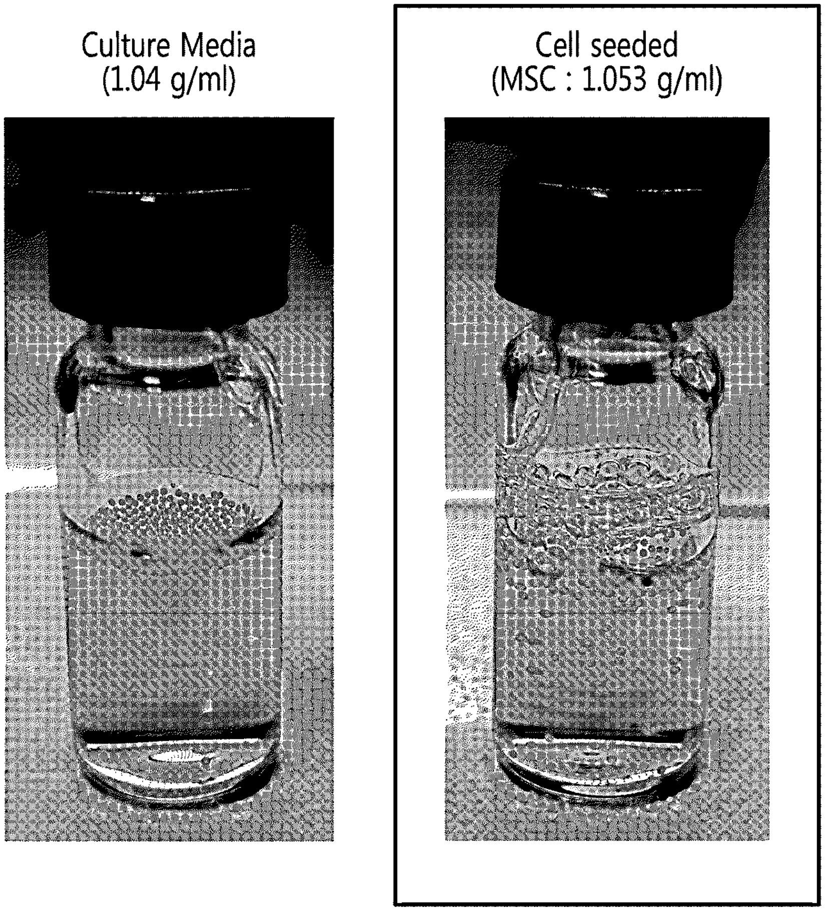
[FIG. 6]
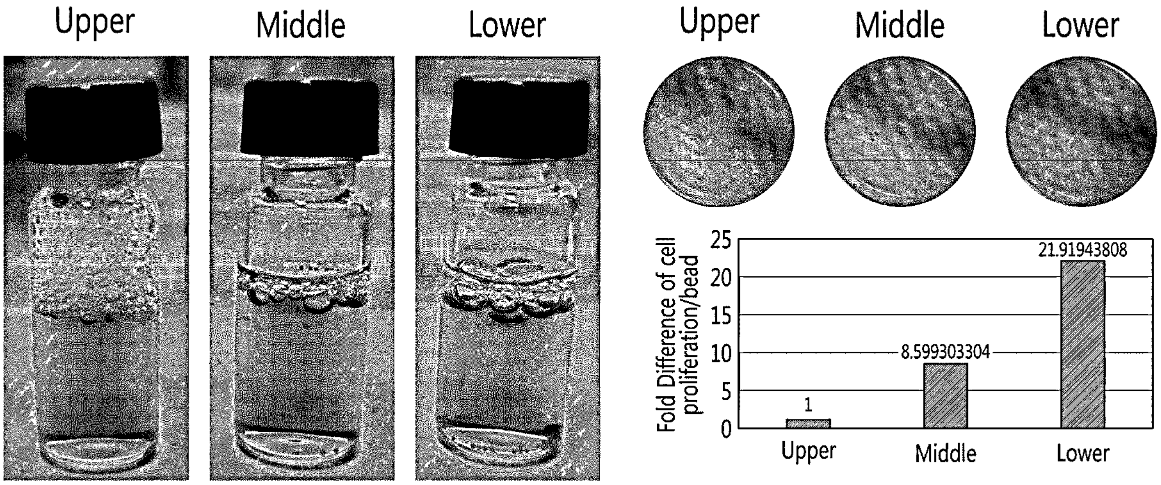

[FIG. 7]
LEFT) POLYSTYRENE MICROCARRIERS (1.04g/cc, 500μm diameter)
RIGHT) LOW SPECIFIC GRAVITY MICROCARRIER (0.995g/cc, 500μm diameter)
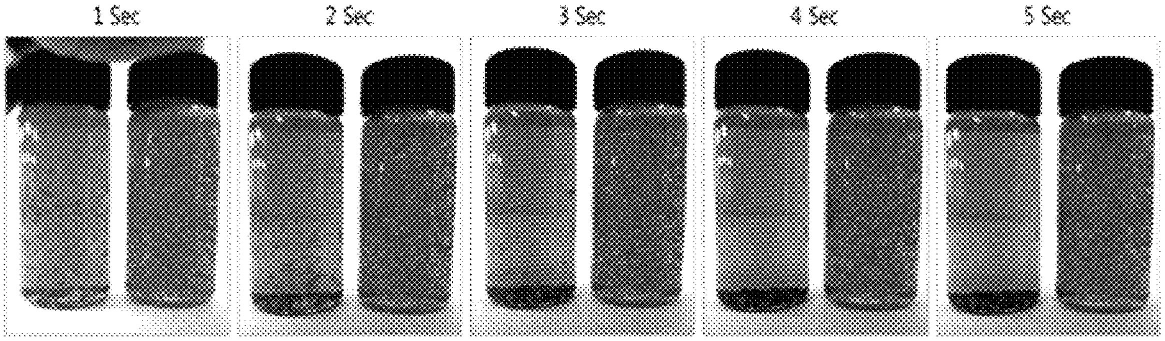

MICROCARRIER BASED-4 DIMENSIONAL CELL CULTURE APPARATUS AND METHOD FOR MONITORING CELL CULTURE USING THE SAME

CROSS REFERENCE TO RELATED APPLICATIONS

This application is a National Stage Entry of PCT International Application No. PCT/KR2021/002775, which was filed on Mar. 5, 2021, and claims priority to Korean Patent Application No. 10-2020-0028471, filed on Mar. 6, 2020, in the Korean Intellectual Property Office, the disclosure of which is incorporated herein by reference.

TECHNICAL FIELD

The present invention relates to a low specific gravity microcarrier-based cell culture apparatus and a method of monitoring cell culture using the same. More particularly, the present invention relates to four-dimensional cell culture that enables monitoring of the growth state of cells by reflecting a time factor in three-dimensional cell culture and is capable of stable cell expansion culture by minimizing change in cell characteristics.

BACKGROUND ART

Recently, regenerative medicine technology for restoring the original function of human cells, tissues, or organs by replacing or regenerating the human cells, tissues, or organs using stem cells or progenitor cells, which are adherent cells, is being actively developed.

Most types of cells derived from solid tissues, except for cancer cells, attach to the surface of glass, plastic, or nylon as a single layer and proliferate on the surface. Research on incubators and culture materials that can provide an environment suitable for in vitro expansion of these cells is being actively conducted.

In particular, a three-dimensional cell culture method that increases a cell adhesion surface using biocompatible microbeads as a support for cell culture is being developed.

By providing a large surface area for cell proliferation, microbeads provide a suitable environment for cells to reside, allowing adherent cells such as stem cells or progenitor cells to grow even in a suspended culture environment.

However, to recover cells, a process of separating cells from the microbeads is required. When separation is performed using centrifugation, since difference in specific gravity between microbeads and cells is insignificant, separation time is increased, which causes damage to the cells. In addition, since a microbead layer and a cell layer are not clearly separated, cells may be lost.

In addition, for safe and efficient cell culture, the types of materials used to manufacture microbeads need to meet the characteristics and purpose of cells culture, and those types of materials are limited. In general, microbeads are made of natural or synthetic polymer materials, and these materials have a specific gravity similar to that of cells.

These materials have a specific gravity of 1.0 to 1.3, and cells or human-derived solid materials have a specific gravity of 1.0 or more. That is, since the polymer materials and the cells or human-derived solid materials have similar specific gravity values, separation using centrifugation is not easy. In addition, when using centrifugation to separate cells and microcarriers, there is a disadvantage in that a filter having micro-sized pores must be additionally used.

In addition, among three-dimensional culture methods developed for in vitro expansion culture of adherent stem cells, the use of plastic microcarrier-based three-dimensional expansion culture, which is evaluated as the best method for expansion culture of adult stem cells, although, microcarriers to which cells are attached remain suspended by continuous stirring. At this time, stirring force generated in the three-dimensional culture acts as physical stress (shear stress) applied to the cells attached to the surface of the microcarriers. This physical stress inhibits cell growth and reduces the activity of the cultured cells.

More specifically, commercially available plastic microcarriers have a higher density than that of a culture medium, so the microcarriers sink quickly during a culture process. Accordingly, to maintain a floating state, continuous stirring must be applied. In this case, physical stress generated and affects the cultured cells attached to the surface of the microcarriers. However, in the three-dimensional cell culture platform, turbulence by stirring is required not only for maintaining the suspension state of the microcarriers, but also for uniform mixing of culture medium components. Therefore, there is a need for a method capable of reducing physical stress applied to cells due to stirring force.

In addition, a plastic microcarrier is in the form of a sphere, and multi-discriminatory characteristics are not implemented according to cell proliferation. Accordingly, the proliferation state of cells cannot be easily grasped. In addition, when observing cells, sampling of microcarriers and special equipment capable of three-dimensional observation are required.

RELATED ART DOCUMENTS

Patent Documents

Korean Patent No. 10-1975100

DISCLOSURE

Technical Problem

Therefore, the present invention has been made in view of the above problems, and it is one object of the present invention to provide a cell culture platform capable of maintaining a suspension state in a three-dimensional space without imparting turbulence by stirring force applied to a cell culture medium by controlling the flow rate of the cell culture medium injected during low specific gravity microcarrier-based three-dimensional cell culture.

Technical Solution

In accordance with one aspect of the present invention, provided is a microcarrier-based cell culture apparatus including a cell culture chamber; a cell culture medium accommodated in the chamber; and microcarriers suspended in the cell culture medium to provide surfaces on which cells are grown.

The cell culture medium may be introduced through a lower region of the cell culture chamber and discharged through an upper region thereof.

A specific gravity of the microcarriers may be less than that of the cell culture medium.

As cells proliferate on surfaces of the microcarriers, the microcarriers may sink to a bottom of the cell culture chamber.

The cell culture chamber may include a turbulent eddy-breaker (150) at a lower end thereof.

In accordance with another aspect of the present invention, provided is a microcarrier-based cell culture monitoring method including a step of providing a cell reactor in which a cell culture medium is introduced through a lower region of a cell culture chamber and the cell culture medium is discharged through an upper region of the cell culture chamber; a cell addition step of adding microcarriers and cells to be grown into the cell culture medium accommodated in the cell culture chamber; and a cell proliferation observation step of confirming change in distribution of cell-microcarrier complexes containing microcarriers having surfaces to which cells to be grown are attached within the cell culture chamber.

The microcarrier-based cell culture monitoring method may further include a step of calculating specific gravity of the cell-microcarrier complexes and may further include a step of deriving data on cell growth state based on the calculated specific gravity of the cell-microcarrier complexes.

Advantageous Effects

According to one aspect of the present invention, since separate stirring force is not required by inducing medium flow through continuous inflow and outflow of a cell culture medium, exposure of cells to physical stress during cell culture can be prevented.

In addition, since physical stress applied to cells is significantly reduced, a similar level of cellular activity can be expected as in two-dimensional cell culture.

In addition, by maintaining the suspension state of microcarriers in three-dimensional cell culture with minimal medium flow, the growth state of cells can be easily monitored based on the distribution position of microcarriers without interfering with change in the distribution of microcarriers according to cell growth.

In addition, a four-dimensional cell culture platform can be provided by implementing change in the behavior of cell-microcarrier complexes according to time change in three-dimensional cell culture.

DESCRIPTION OF DRAWINGS

FIG. 1 schematically illustrates a cell culture apparatus according to an embodiment of the present invention.

FIG. 2A schematically illustrates a microcarrier-based cell culture apparatus without a turbulent eddy-breaker, and FIG. 2B schematically illustrates a cell culture apparatus including a turbulent eddy-breaker according to an embodiment of the present invention.

FIG. 3A shows distribution of cells (cell-microcarrier complexes) and nutrients according to a vertical (height) gradient in a cell culture apparatus according to an embodiment of the present invention.

FIG. 3B shows distribution of cells and nutrients according to a vertical (height) gradient in a two-dimensional cell culture dish according to a comparative example of the present invention.

FIG. 4 schematically illustrates a four-dimensional cell culture according to an embodiment of the present invention.

FIG. 5 shows microcarriers included in a microcarrier-based cell culture apparatus according to an embodiment of the present invention.

FIG. 6 shows the degree of proliferation of microcarrier surface cells according to the positional behavior of microcarriers included in a microcarrier-based cell culture apparatus according to an embodiment of the present invention.

FIG. 7 shows the time-dependent behaviors of microcarriers made of polystyrene and microcarriers included in a microcarrier-based cell culture apparatus according to an embodiment of the present invention.

BEST MODE

The present invention will now be described more fully with reference to the accompanying drawings and contents disclosed in the drawings. However, the present invention should not be construed as limited to the exemplary embodiments described herein.

The terms used in the present specification are used to explain a specific exemplary embodiment and not to limit the present inventive concept. Thus, the expression of singularity in the present specification includes the expression of plurality unless clearly specified otherwise in context. It will be further understood that the terms "comprise" and/or "comprising", when used in this specification, specify the presence of stated components, steps, operations, and/or elements, but do not preclude the presence or addition of one or more other components, steps, operations, and/or elements thereof.

It should not be understood that arbitrary aspects or designs disclosed in "embodiments", "examples", "aspects", etc. used in the specification are more satisfactory or advantageous than other aspects or designs.

Although terms used in the specification are selected from terms generally used in related technical fields, other terms may be used according to technical development and/or due to change, practices, priorities of technicians, etc. Therefore, it should not be understood that terms used below limit the technical spirit of the present invention, and it should be understood that the terms are exemplified to describe embodiments of the present invention.

Also, some of the terms used herein may be arbitrarily chosen by the present applicant. In this case, these terms are defined in detail below. Accordingly, the specific terms used herein should be understood based on the unique meanings thereof and the whole context of the present invention.

Meanwhile, terms such as "first" and "second" are used herein merely to describe a variety of constituent elements, but the constituent elements are not limited by the terms. The terms are used only for the purpose of distinguishing one constituent element from another constituent element.

In addition, when an element such as a layer, a film, a region, and a constituent is referred to as being "on" another element, the element can be directly on another element or an intervening element can be present.

Unless defined otherwise, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

In addition, in the following description of the present invention, a detailed description of known functions and configurations incorporated herein will be omitted when it may make the subject matter of the present invention unclear. The terms used in the specification are defined in consideration of functions used in the present invention, and can be changed according to the intent or conventionally used methods of clients, operators, and users. Accordingly, definitions of the terms should be understood on the basis of the entire description of the present specification.

Hereinafter, embodiments of the present invention will be described in detail with reference to the accompanying drawings.

FIG. 1 schematically illustrates a microcarrier-based cell culture apparatus according to an embodiment of the present invention.

Referring to FIG. 1, a microcarrier-based cell culture apparatus 100 according to one aspect of the present invention includes a cell culture chamber 110; a cell culture medium 120 accommodated in the cell culture chamber 110; and microcarriers 131 that provide surfaces on which cells 133 grow while floating in the cell culture medium 120.

Accordingly, the microcarrier-based cell culture apparatus 100 according to one aspect of the present invention is capable of culturing all adherent cells, including epidermal cells, fibroblasts, mesenchymal stem cells, and chondrocytes.

Through-holes 140 through which the cell culture medium is introduced and discharged may be provided in the upper and lower regions of the cell culture chamber 110, respectively. More specifically, the through-holes 140 through which the cell culture medium 120 is introduced and discharged may be formed on the sides of the cell culture chamber 110. More specifically, a through-hole 141 through which the cell culture medium 120 is introduced may be provided in a lower region of one side of the cell culture chamber 110, and a through-hole 142 through which the cell culture medium 120 is discharged may be provided in an upper region of the other side of the cell culture chamber 110.

The cell culture medium 120 is a fluid containing nutrients required for growth or proliferation of the cells 133 as a culture medium in the cell culture chamber 110.

The cell culture medium 120 is introduced through a lower region of the cell culture chamber 110 and is discharged through an upper region of the cell culture chamber 110. The cell culture medium 120 may form a fluid flow in the cell culture chamber 110. More specifically, the cell culture medium 120 may form a medium flow from the bottom of the cell culture chamber 110 to the top thereof.

The cell culture medium 120 may be introduced through a lower region of one side of the cell culture chamber 110 and the introduced cell culture medium 120 may be discharged through an upper region of the other side of the cell culture chamber 110. Accordingly, the cell culture medium 120 forms a medium flow in the direction from bottom to top in the cell culture chamber 110, and the direction of the medium flow is opposite to the movement direction of the sinking microcarriers 131 or sinking cell-microcarrier complexes 130 to described later. Accordingly, by this medium flow, the suspension state of the microcarriers 131 or the cell-microcarrier complexes 130 in the cell culture chamber 110 may be maintained.

The medium flow from bottom to top formed by the cell culture medium 120 may replace stirring force required to evenly disperse and suspend microcarriers in a conventional cell culture apparatus. Accordingly, since separate stirring force is not required for cell culture, cells may be grown without being subjected to physical stress. The suspension state of the cell-microcarrier complexes 130 or the microcarriers 131 may be maintained only by the medium flow in the cell culture chamber 110. At the same time, change in distribution positions according to increase in the specific gravity of the cell-microcarrier complexes 130 to be described later is not hindered. Accordingly, by checking the distribution positions of the cell-microcarrier complexes 130, the growth state of the cells 133 of the cell-microcarrier complexes 130 may be intuitively checked.

Since the cell culture medium 120 is continuously introduced into the cell culture chamber 110 and continuously discharged from the cell culture chamber 110, nutrients necessary for the growth of the cells 133 in the cell culture chamber 110 may be continuously supplied.

The microcarrier 131 is a micrometer-scale bead particle, and the cells 133 attach and grow on the surface thereof. The microcarrier 131 have cell culture stability and is made of a biocompatible and biologically stable material.

The microcarriers 131 may have a sphere or disk shape, and the cells 133 may be attached to the surfaces of the microcarriers 131 to form the cell-microcarrier complexes 130.

The cells 133 are attached to the surfaces of the microcarriers 131 to form the cell-microcarrier complexes 130. The cells 133 attached to the surfaces of the microcarriers 131 may grow or proliferate. More specifically, the cells 133 grow or proliferate on the entire three-dimensional surface of the spherical or disk-shaped microcarrier 131. By attaching and culturing (growing) the cells 133 on the three-dimensional surfaces, three-dimensional cell culture in the form of a colony may be performed in vitro under an environment similar to that of a living body.

As the cells 133 on the surfaces of the microcarriers 131 grow, the specific gravity of the cell-microcarrier complexes 130 increases. Due to the increased specific gravity, the cell-microcarrier complexes 130 may sink to the bottom of the cell culture chamber 110.

The specific gravity of the microcarriers 131 may be less than that of the cell culture medium 120. The microcarriers 131 may be made of a material having a specific gravity less than that of the cell culture medium 120. The microcarriers 131 exhibit the behavioral characteristics of a relatively light material in the cell culture medium 120. Accordingly, the microcarriers 131 or the cell-microcarrier complexes 130 may be suspended by a very small medium flow formed by the cell culture medium 120. At the same time, location distribution according to increase in the specific gravity of the cell-microcarrier complexes 130 may be confirmed. The growth state of the cells 133 of the cell-microcarrier complexes 130 may be intuitively confirmed through confirmation of the location distribution.

The specific gravity of the cells 133 growing while attached to the surfaces of the microcarriers 131 may be greater than that of the cell culture medium 120. Depending on the type of cells to be cultured, the specific gravity values of the cell culture medium and the microcarriers may be determined.

For example, common cell culture media have a specific gravity of 1.04 to 1.20. Thus, microcarriers having a specific gravity less than that of a cell culture medium may have a specific gravity of 1.02 or less. More specifically, in the case of bone marrow stromal cells (BMSCs) having a specific gravity of 1.053, a cell culture medium having a specific gravity of 1.04 may be used, and microcarriers having a specific gravity of 1.0 or less may be used. Meanwhile, when the specific gravity value of the microcarrier beads is too small, the microcarrier beads in a cell culture medium may maintain a suspension state, but change in the specific gravity of the microcarriers according to cell proliferation may be insignificant. Thus, it is preferable to use microcarriers having a specific gravity of 0.775 or more.

FIG. 2A schematically illustrates a microcarrier-based cell culture apparatus without a turbulent eddy-breaker, and FIG. 2B schematically illustrates a cell culture apparatus including a turbulent eddy-breaker according to an embodiment of the present invention.

FIG. 2B includes the same components as the cell culture apparatus according to an embodiment of the present invention shown in FIG. 1, and thus description of the same components will be omitted.

FIG. 2A shows a microcarrier-based cell culture apparatus without a turbulent eddy-breaker. In this case, due to large eddies formed when the cell culture medium 120 is injected from the bottom, it is difficult to confirm the overall suspension behavior of the cell-microcarrier complexes 130 according to change in the specific gravity of the cell-microcarrier complexes 130.

Referring to FIG. 2A, the through-hole 141 (e.g., inlet) through which the cell culture medium 120 is introduced is formed at a lower region of the cell culture chamber 110. Compared to the size of the cell culture chamber 110, the diameter of the through-hole 141 is relatively small. Thus, large eddies formed immediately after the cell culture medium 120 is introduced gradually become smaller, thereby forming turbulent eddies. Consequently, the entire cell culture chamber 110 is filled with turbulent eddies. In this case, it is difficult to detect a subtle change in the specific gravity of the cell-microcarrier complexes 130 according to cell growth.

On the other hand, referring to FIG. 2B, in the case of the cell culture apparatus including a turbulent eddy-breaker according to an embodiment of the present invention, by installing a turbulent eddy-breaker 150 at a lower end of the cell culture chamber 110 into which the cell culture medium 120 is introduced, formation of large eddies by inflow of the cell culture medium 120 may be prevented, and turbulent eddies may be turned into small eddies, thereby forming a stable flow along the bottom-top axis in the cell culture chamber 110.

That is, in the cell culture apparatus including a turbulent eddy-breaker according to an embodiment of the present invention, due to a stable flow of the cell culture medium 120 by the turbulent eddy-breaker, the cell-microcarrier complexes 130 exhibiting high cell proliferation are positioned at the bottom of the cell culture chamber 110, and thus the fresh cell culture medium 110 may be supplied to the cells smoothly. In addition, the cell-microcarrier complexes 130 exhibiting low cell proliferation may be distributed at the top of the cell culture chamber 110.

The turbulent eddy-breaker 150 has a structure filled with beads so that the cell culture medium 120 flows between the beads. For example, the beads may include any one of glass beads, titanium beads, and stainless steel beads, without being limited thereto.

In addition, the cell culture apparatus 100 according to an embodiment of the present invention shown in FIG. 2B may be used to monitor four-dimensional cell culture.

FIG. 3A shows distribution of the cells 133 (or the cell-microcarrier complexes 130) ("Cell density" of FIG. 3A) and distribution of nutrients contained in the cell culture medium 120 ("Media nutrient gradient" of FIG. 3A) according to the vertical (height) gradient (left image of FIG. 3A) in the cell culture apparatus 100 according to an embodiment of the present invention shown in FIG. 1.

FIG. 3B is a comparative example of the present invention and shows distribution of cells ("Cell density" of FIG. 3B) and distribution of nutrients ("Media nutrient gradient" of FIG. 3B) contained in a cell culture medium according to the vertical (height) gradient of the cell culture medium during cell culture (two-dimensional cell culture) on the bottom (left image of FIG. 3B).

Referring to FIGS. 1 and 3A, the cells 133 attached to the surfaces of the microcarriers 131 grow while consuming nutrients contained in the cell culture medium 120. At the initial stage of cell culture, the number of cells attached to the surfaces of the microcarriers 131 is small, and cell growth begins. Thus, a large number of cell-microcarrier complexes 130 and microcarriers 131 exist in a suspended state in an upper region of the cell culture medium 120.

As the cell culture progresses, the cells 133 attached to the surfaces of the microcarriers 131 grow, thereby increasing the specific gravity of the cell-microcarrier complexes 130. The cell-microcarrier complexes 130 having an increased specific gravity sink to the bottom of the cell culture chamber 110.

Since the cell-microcarrier complexes 130 having an increased specific gravity sink to the bottom of the cell culture chamber 110, the density of the cell-microcarrier complexes 130 increases from the top to the bottom of the cell culture medium 120 over cell culture time.

At this time, as the cell culture medium 120 is continuously introduced through the bottom of the cell culture chamber 110, the content of nutrients in the cell culture medium 120 at the bottom of the cell culture chamber 110 is continuously increased. In the upper region of the cell culture medium 120, as cells attached to the cell-microcarrier complexes grow, nutrients are continuously consumed, and the cell culture medium 120 in which nutrients are consumed is discharged through the top of the cell culture chamber 110. Thus, the content of nutrients in the cell culture medium 120 increases from the top to the bottom of the cell culture medium 120. The distribution of nutrients is similar to the distribution of cells of the cell-microcarrier complexes 130 in the cell culture chamber 110.

Accordingly, the distribution pattern of the cell-microcarrier complexes 130 and the distribution pattern of nutrients in the cell culture medium 120 are the same and show a vertical (height) gradient in the cell culture chamber 110. Thus, a cell culture environment that allows cells of the cell-microcarrier complexes 130 to grow effectively may be provided.

In addition, in the three-dimensional cell culture using the microcarriers 131, as culture time elapses, the specific gravity of the cell-microcarrier complexes 130 increases, and thus the cell-microcarrier complexes 130 sink in the cell culture medium 120. The cell culture medium 120 is introduced through the bottom of the cell culture chamber 110, and thus the content of nutrients at the bottom of the cell culture chamber 110 is increased. Accordingly, four-dimensional cell culture using space-time that allows continuous cell growth over time may be provided.

In contrast, referring to FIG. 3B, as a comparative example, in the case of a two-dimensional cell culture apparatus in which a medium flow is not formed due to the absence of continuous inflow and outflow of a cell culture medium in a cell culture chamber, and cells are fixed to the bottom surface of the cell culture chamber, since cells grow and proliferate only in the lower region of the cell culture medium, the cells are distributed only in the lower region. Accordingly, nutrients present in the lower region of the cell culture medium are rapidly consumed. Consequently, the upper region of the cell culture medium has a high nutrient content, but the lower region thereof has a low nutrient content. Thus, due to consumption of nutrients contained in the cell culture medium in the lower region, cells located at the bottom grow slowly.

FIG. 4 schematically illustrates four-dimensional cell culture using the cell culture apparatus 100 according to an embodiment of the present invention.

Referring to FIG. 4, when a cell culture medium 220 has a density of about 1.04 g/ml, microcarriers 231 have a density of about 0.98 g/ml, and cells 233 has a density of about 1.07 g/ml, the cells 233 are attached to the microcarriers 231 located on the surface layer of the cell culture medium 220 over time to form cell-microcarrier complexes 230, and the cell-microcarrier complexes 230 having an increased density due to growth of the cells 233 sink.

In addition, in the cell culture apparatus 100 of the present invention, as the cell culture medium 120 moves from the bottom to the top of the cell culture chamber 110, the distribution of the cell-microcarrier complexes 130 is changed according to the degree of cell growth in the cell culture chamber 110, and the degree of growth of the cells 133 may be intuitively determined based on the changed distribution.

A microcarrier-based cell culture monitoring method according to one aspect of the present invention is a method of monitoring cell culture using the cell culture apparatus according to one aspect of the present invention, and repeated descriptions of a cell culture apparatus, a cell culture medium, microcarriers, cells, and cell-microcarrier complexes will be omitted.

The microcarrier-based cell culture monitoring method includes a step of providing a cell reactor in which a cell culture medium is introduced through a lower region of a cell culture chamber and the cell culture medium is discharged through an upper region of the cell culture chamber; a cell addition step of adding microcarriers and cells to be grown into the cell culture medium accommodated in the cell culture chamber; and a cell proliferation observation step of confirming change in distribution within the cell culture chamber of cell-microcarrier complexes containing microcarriers having surfaces to which cells to be grown are attached.

The cell proliferation observation step may be a step of observing change in location distribution over time or may be a step of observing change in the height of the cell-microcarrier complexes sinking in the cell culture medium due to increase in the specific gravity of the cell-microcarrier complexes.

In addition, the microcarrier-based cell culture monitoring method may further include a step of calculating the specific gravity of the cell-microcarrier complexes.

In addition, the microcarrier-based cell culture monitoring method may further include a step of deriving data on cell growth state based on the calculated specific gravity of the cell-microcarrier complexes. More specifically, the specific gravity of grown cells may be calculated based on difference in specific gravity between the microcarriers and the cell-microcarrier complexes, and the degree of cell growth may be determined based on difference in specific gravity between the grown cells and the cells added in the cell addition step.

When the microcarrier-based cell culture monitoring method is used, the degree of cell growth or proliferation may be predicted according to the degree of sinking of the cell-microcarrier complexes in the cell proliferation observation step. In addition, the method allows for dynamic analysis and real-time monitoring of cell growth by taking a time factor into account.

Preparation Examples

Since the surface of polyethylene (0.91 to 0.96 g/cm$^3$), which is a plastic material having a relatively low density compared to water, exhibits hydrophobicity, to enable dispersion of polyethylene in an aqueous solution environment, which is the growth environment of cells, the surface of polyethylene was converted from hydrophobic to hydrophilic through surface modification (Note: the density of polypropylene is 0.855 to 0.946 g/cm$^3$).

As a polyethylene core (bead) used in the experiment, a core having a density of 0.99 g/ml or 0.995 g/ml containing a rhodamine B fluorescent molecule was used. Here, the diameter of the polyethylene core was about 500 μM.

To perform surface etching of the polyethylene core, a solution containing distilled water, 30% ammonia water, and 30% hydrogen peroxide in a ratio of 5:1:1 was placed in a glass vial, and the glass vial was placed in a water bath at 70° C. for 2 hours. At this time, the glass vial was shaken every 10 minutes to disperse the polyethylene core.

Before the reaction, the polyethylene core floated on the surface of the aqueous solution while the surface of the polyethylene core was not wetted. After the reaction, the surface property was changed to hydrophilicity, the core covering the surface of the aqueous solution was separated, and surface modification reaction was performed using a trimethoxy aminopropylsilane solution.

The diameter of the spherical microbeads surface-modified with trimethoxy aminopropylsilane was about 500 μm.

340 surface-modified microbeads having a diameter of 500 μM and 3.5x10$^2$ mesodermal stem cells were added to a plastic tube and mixed. Temperature was maintained at 37° C. so that the cells were attached to the surfaces of the microbeads. At this time, to uniformly attach the cells to the microbeads, the tube was incubated at 37° C. for 2 hours while shaking every 10 minutes.

FIG. 5 illustrates microcarriers included in a microcarrier-based cell culture apparatus according to an embodiment of the present invention.

In a state that the polyethylene core whose surface characteristics have been changed to hydrophilic through surface etching is present in the upper layer of a culture medium, mesodermal stem cells were added at a density of 7.5x10$^3$ cells/cm$^2$ per microcarrier surface area, and the test tube of FIG. 5 was incubated overnight while inverting at a speed of 20 rpm so that the cells were attached to the surfaces of the microcarriers.

Referring to FIG. 5, before cell seeding, low specific gravity microcarriers were located at an upper layer of a cell culture medium (Culture Media). At the time of incubating for 16 hours (overnight) after cell seeding, the microcarriers were evenly dispersed throughout the cell culture medium (Cell seeded).

FIG. 6 shows the degree of proliferation of microcarrier surface cells according to the positional behavior of microcarriers included in a microcarrier-based cell culture apparatus according to an embodiment of the present invention.

After seeding mesodermal stem cells in the same manner as in FIG. 5, the mesodermal stem cells were incubated for 48 hours. Then, according to the distribution position of cell-microcarrier complexes in a culture medium, the cell-microcarrier complexes were divided into (1) a fraction located on the surface of the culture medium (Upper), (2) a fraction evenly dispersed in the culture medium (Middle), and (3) a fraction sinking to the bottom of the culture vial (Lower). As shown in FIG. 6, while maintaining the culture state in the same volume of culture medium, MTT assay (cytotoxicity and cell viability test) was performed to compare the number of viable cells for each fraction.

Referring to FIG. 6, in the fraction sinking to the lower region of the cell culture medium, the number of cell-microcarrier complexes was the lowest (in the upper-right), but the number of cells was the highest. In the fraction located in the upper region of the cell culture medium, the number of cell-microcarrier complexes was the highest, but the number of cells was the lowest.

Accordingly, by confirming the behavior of the cell-microcarrier complexes in the cell culture medium, it was possible to intuitively monitor the proliferation state of the cells.

FIG. 7 shows the time-dependent behaviors of microcarriers made of polystyrene and microcarriers included in a microcarrier-based cell culture apparatus according to an embodiment of the present invention.

As shown in FIG. 7, different types of microcarriers were placed in test tubes containing a cell culture medium, respectively. The test tubes were shaken to disperse the microcarriers evenly. Then, the test tubes were placed on a test bench and the distribution behavior of the microcarriers over time was observed. Conventionally used microcarriers made of polystyrene (density of 1.04 g/ml or more) sank to the bottom of the test tube containing the cell culture medium within 3 seconds. The low specific gravity microcarriers having a density of 0.995 g/ml were uniformly dispersed over 5 seconds. In addition, the low specific gravity microcarriers were evenly dispersed in 50% or more of the total volume up to 30 seconds.

That is, the microcarrier-based cell culture apparatus according to an embodiment of the present invention is capable of maintaining the suspension state of cell-microcarrier complexes by applying a minimum of stirring force in a cell culture chamber.

Meanwhile, embodiments of the present invention disclosed in the present specification and drawings are only provided to aid in understanding of the present invention and the present invention is not limited to the embodiments. It will be apparent to those skilled in the art that various modifications can be made to the above-described exemplary embodiments of the present invention without departing from the spirit and scope of the invention.

The invention claimed is:

1. A microcarrier-based cell culture apparatus, comprising:

a cell culture chamber;

a cell culture medium accommodated in the chamber; and microcarriers suspended in the cell culture medium to provide surfaces on which cells are grown, wherein the cell culture medium is introduced through a lower region of the cell culture chamber and discharged through an upper region thereof, wherein, as cells grow on surfaces of the microcarriers, a specific gravity of cell-microcarrier complexes each comprising a respective microcarrier and cells attached thereto increases such that the cell-microcarrier complexes sink toward a bottom region of the cell culture chamber, and a growth state of the cells is observed by confirming a change in location distribution within the cell culture chamber of the cell-microcarrier complexes, wherein the cell culture chamber comprises a turbulent eddy-breaker at a lower end thereof, and the turbulent eddy-breaker prevents formation of large eddies generated by inflow of the cell culture medium and turns the turbulent eddies into small eddies such that a stable flow is formed along a bottom-top axis of the cell culture chamber.

2. The microcarrier-based cell culture apparatus according to claim 1, wherein a specific gravity of the microcarriers is less than that of the cell culture medium.

3. The microcarrier-based cell culture apparatus according to claim 2, wherein, as cells proliferate on surfaces of the microcarriers, the microcarriers sink to a bottom of the cell culture chamber.

* * * * *